United States Patent
E et al.

(10) Patent No.: US 12,264,292 B2
(45) Date of Patent: Apr. 1, 2025

(54) LUBRICATING OIL FRICTION MODIFIER AND PREPARATION METHOD THEREFOR AND APPLICATION THEREOF

(71) Applicant: CHINA PETROLEUM & CHEMICAL CORPORATION, Beijing (CN)

(72) Inventors: Hongjun E, Beijing (CN); Xueling Du, Beijing (CN); Hu Xin, Beijing (CN); Ling Lei, Beijing (CN); Cheng Li, Beijing (CN); Dandan Jiang, Beijing (CN); Jiajia Jin, Beijing (CN); Ahebota Baheti, Beijing (CN)

(73) Assignee: CHINA PETROLEUM & CHEMICAL CORPORATION, Beijing (CN)

( * ) Notice: Subject to any disclaimer, the term of this patent is extended or adjusted under 35 U.S.C. 154(b) by 0 days.

(21) Appl. No.: 18/577,522

(22) PCT Filed: Jan. 26, 2022

(86) PCT No.: PCT/CN2022/074009
§ 371 (c)(1),
(2) Date: Jan. 8, 2024

(87) PCT Pub. No.: WO2023/279707
PCT Pub. Date: Jan. 12, 2023

(65) Prior Publication Data
US 2024/0263097 A1 Aug. 8, 2024

(30) Foreign Application Priority Data
Jul. 6, 2021 (CN) .......................... 202110761894.6

(51) Int. Cl.
*C10M 169/04* (2006.01)
*C10M 149/00* (2006.01)
*C10N 20/00* (2006.01)

(52) U.S. Cl.
CPC ...... *C10M 169/041* (2013.01); *C10M 149/00* (2013.01); *C10M 2213/06* (2013.01); *C10M 2217/046* (2013.01); *C10N 2020/075* (2020.05)

(58) Field of Classification Search
CPC .......... C10M 169/041; C10M 2213/06; C10M 2217/046; C10M 2201/081;
(Continued)

(56) References Cited

U.S. PATENT DOCUMENTS 5,453,539 A * 9/1995 Kondo ................... G11B 5/735
508/517

FOREIGN PATENT DOCUMENTS

| CN | 102414251 A | 4/2012 |
|----|-------------|--------|
| CN | 108264956 A | 7/2018 |

(Continued)

OTHER PUBLICATIONS

Ding, Ling et al.; "Ionic Liquids as Novel Lubricants"; Progress in Chemisry; vol. 22, No. 2/3, Mar. 24, 2010; ISSN:1005-281X; pp. 298-308.

*Primary Examiner* — Taiwo Oladapo
(74) *Attorney, Agent, or Firm* — NKL Law; Allen Xue

(57) ABSTRACT

A lubricating oil friction modifier and a preparation method therefor and use thereof are provided. The lubricating oil friction modifier has a chemical formula of $A_x B^{y+}(C^-)_y$. In the formula, A is a perfluoropolyether acyl group, $B^{y+}$ represents a cationic group having x amino groups and y ammonium ions, $C^-$ is $BF_4^-$, $PF_6^-$, $AsF_6^-$, $FAP^-$, $TFSI^-$, $Mn_2O_4$ or $ClO_4^-$, x is an integer greater than or equal to 1, y is an integer greater than or equal to 1, and x+y≥2. The
(Continued)

lubricating oil friction modifier has a good solubility with fluorine oil and fluorine grease, will not precipitate in the fluorine oil and the fluorine grease after being added, and can significantly improve the wear resistance of a lubricating oil such as the fluorine oil and the fluorine grease.

18 Claims, 1 Drawing Sheet

(58) Field of Classification Search
CPC .......... C10M 2215/04; C10M 2215/08; C10M 147/00; C10M 149/14; C10M 135/10; C10M 161/00; C10M 169/044; C10M 2217/06; C10M 2219/044; C10N 2020/075; C10N 2020/077; C10N 2050/10; C10N 2030/06; C07C 217/00; C08G 83/00; C08G 83/004
See application file for complete search history.

(56) References Cited

FOREIGN PATENT DOCUMENTS

| | | |
|---|---|---|
| CN | 111233664 A | 6/2020 |
| EP | 1632516 A2 | 3/2006 |
| WO | 2010112233 A1 | 10/2010 |

\* cited by examiner

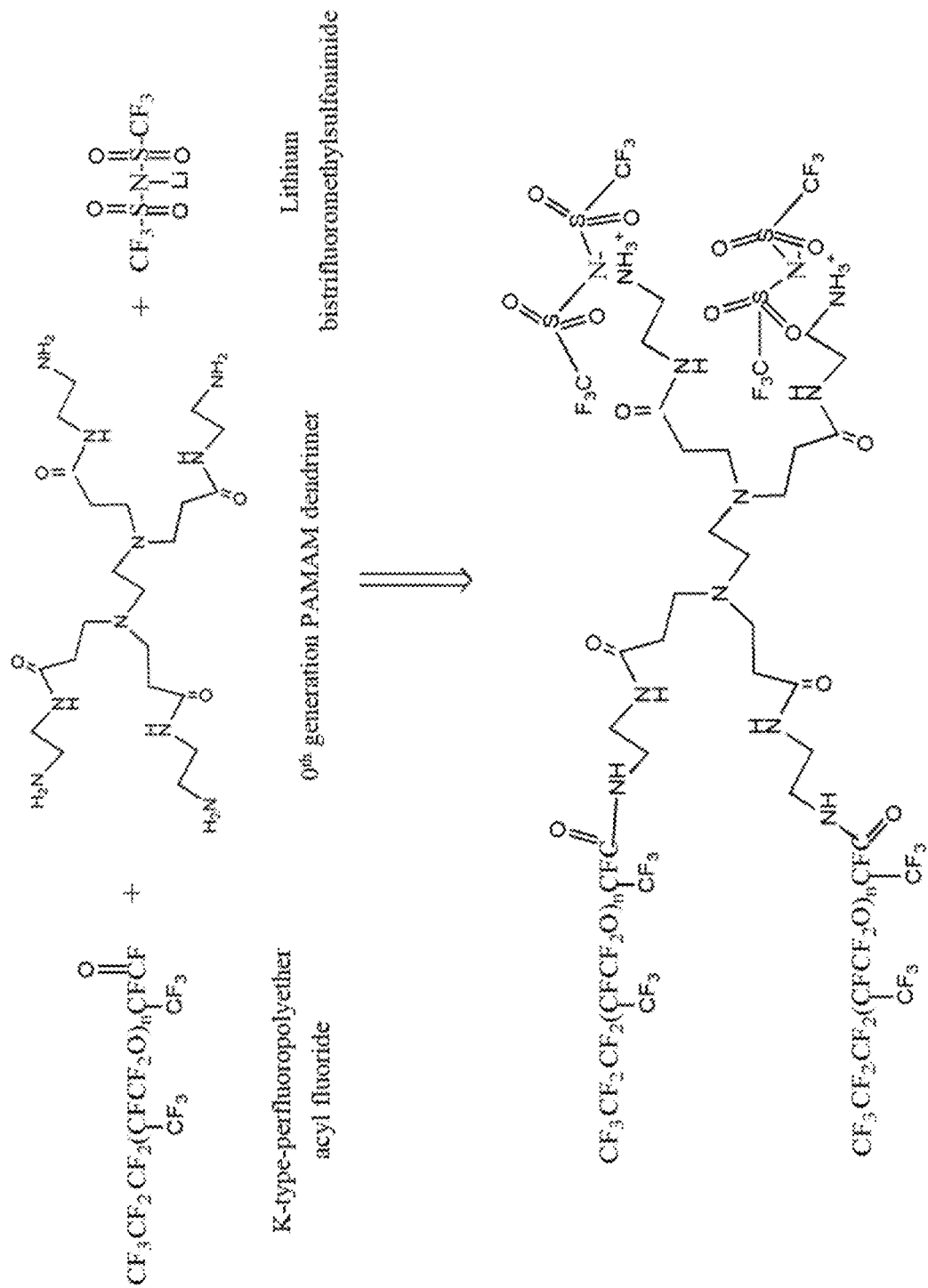

LUBRICATING OIL FRICTION MODIFIER AND PREPARATION METHOD THEREFOR AND APPLICATION THEREOF

CROSS-REFERENCE TO RELATED APPLICATIONS

The present application is a U.S. national stage entry of PCT international application no. PCT/CN2022/074009, filed on Jan. 26, 2022, which claims the priority to Chinese patent application No. 202110761894.6 entitled "Lubricating oil friction modifier and preparation method therefor and application thereof" and filed on Jul. 6, 2021, the content of which is incorporated herein by reference in its entirety.

FIELD OF THE INVENTION

The present invention belongs to the technical field of lubricating oil, and in particular relates to a lubricating oil friction modifier and a preparation method therefor and application thereof.

BACKGROUND OF THE INVENTION

The fluorine chemical industry emerged in the 1930s. The fluorine compounds have received widespread attention due to their unique performances, and have been rapidly applied in the fields of textiles, electronics, aerospace, semiconductors, medical treatment, etc. With the development of science and technology, more and more fluorine-containing fine chemical products have been developed, and their application fields have become more and more extensive. The fluorine chemical products have become common chemical products in daily life, and the fluorine chemical industry has also become an important branch in the chemical industry.

The fluorine chemical products include inorganic fluorine compounds and organic fluorine compounds. The inorganic fluorine compounds include hydrofluoric acid, oxidized fluorides, fluorine-containing gases, fluoride salts, etc. There are approximately a hundred types of inorganic fluorine products in the worldwide, and the inorganic fluorine compounds are still the main products in Chinese fluorine chemical industry. The organic fluorine compounds are developed on the basis of the inorganic fluorine compounds, and mainly include ODS and its substitutes, fluorine rubbers, fluorine coatings, and fluorine-containing fine chemicals. With the continuous development of the fluorine chemical industry, the fluorine-containing fine chemical products with unique performances have played an important supporting role in the industries of aerospace, automotive, medicines, electronic and electrical industries, etc., for example, a perfluoropolyether oil which is applied in a spacecraft. At the same time, the rapid development of the economy has provided a broad application space for the application of the fluorine-containing fine chemical products. There are over 10000 types of fluorine-containing fine chemical products in the worldwide, and the output value thereof accounts for 70% in the fluorine chemical industry, such that they have become a research hot spot in the fluorine chemical industry and even in the entire chemical industry.

The fluorine oil has increasingly received attention due to its performances such as high stability, oxidation resistance, corrosion resistance, etc. At present, the fluorine oil has been widely used in the fields of textiles, chemical industry, electronics, electricals, mechanicals, nuclear industry, aerospace media, magnetic media, etc. The fluorine oil is a special lubricating oil that cannot be replaced in extreme environments; and the main foreign manufacturers thereof include DuPont in USA, Daikin in Japan, and Montefluos Company in Italy, with an annual output of several hundred thousand kilograms of fluorine oil, which is mainly sold to developed countries such as Western Europe, Japan, etc. The yield and variety of the fluorine oil are increasing. There are over 6000 types of fluorocarbon surfactants obtained by modifying the fluorine oil, and the products are developing towards serialization, functionalization and generalization. In China, at present, domestic companies such as Sinopec Lubricant Co., Ltd., Shanghai Aiken Chemical Technology Co., Ltd., and Fujian Yonghong High-tech Co., Ltd., etc. only have a small quantity of perfluoropolyether oil products for sale, with very few product varieties and a significant gap in product quality as compared to foreign countries.

The synthesis technology of fluorine oil has always been a highly confidential trade secret for related enterprises. At the same time, it is difficult for a single fluorine oil to meet the lubrication need under harsh conditions in nuclear industry, aerospace industry, military industry, etc. For this purpose, it is necessary to add additives to fluorine oil to supplement and improve its property requirements. Due to the limited solubility of fluorine oil, there are few additives that may be added to improve its performances. The dispersion and stability of additives in fluorine-containing oil have become one of the main problems limiting its applications. However, these oil soluble additive technologies are controlled by foreign companies, which becomes a bottleneck problem that restricts the profound development of national lubrication technologies. At present, high-performance fluorine oil and fluorocarbon surfactants in China still mainly rely on imports. In the market, only DuPont and Solvay companies sell fluorine-containing additives, and these additives are directly added to fluorine oil so as to prevent the technological leakage of fluorine-containing additives. Therefore, it is necessary to amplify the research and development efforts of high-performance fluorine oil and related products to meet the growing market demand.

SUMMARY OF THE INVENTION

In view of this, the objective of the present invention is to provide a lubricating oil friction modifier and a preparation method therefor and application thereof, in response to the technical problems existing in the prior art. The lubricating oil friction modifier of the present invention has a good solubility with fluorine oil and fluorine grease, will not precipitate in the fluorine oil and the fluorine grease after being added, and can significantly improve the wear resistance of a lubricating oil such as the fluorine oil and the fluorine grease.

The objective of the present invention is achieved by the following technical solutions.

In a first aspect, the present invention provides a lubricating oil friction modifier, having a chemical formula of $A_xB^{y+}(C^-)_y$, wherein A represents a perfluoropolyether acyl group, $B^{y+}$ represents a cationic group having x amino groups and y ammonium ions ($-NH_3^+$), $C^-$ is $BF_4^-$ (boron tetrafluoride anion), $PF_6^-$ (hexafluorophosphate anion), $AsF_6^-$ (hexafluoroarsenate anion), trifluorotri(pentafluoroethyl) phosphate anion ($FAP^-$, its structure is represented by formula V), bistrifluoromethylsulfonimide anion ($TFSI^-$), $Mn_2O_4^-$ (manganate) or $ClO_4^-$ (perchlorate), x is an integer greater than or equal to 1, y is an integer greater than or equal to 1, and x+y≥2.

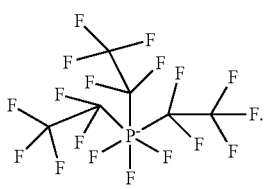 [SMILES: FC(F)(F)C(F)(F)[P-](F)(F)(F)(C(F)(F)C(F)(F)F)C(F)(F)C(F)(F)F]

In the present invention, a group A is linked to an amino group in $B^{y+}$ via a covalent bond to form an amide group (—CONH—), while $C^-$ is linked to an ammonium ion in $B^{y+}$ via an ionic bond. The inventor of the present application found that the lubricating oil friction modifier having the chemical formula $A_xB^{y+}(C^-)_y$ has a good solubility in lubricating oils of fluorine oil and fluorine grease, will not precipitate in the fluorine oil and the fluorine grease after being added, and can significantly improve the wear resistance of a lubricating oil such as the fluorine oil and the fluorine grease.

According to the lubricating oil friction modifier provided by the present invention, wherein, A is a group represented by formulae K, Y, Z or D:

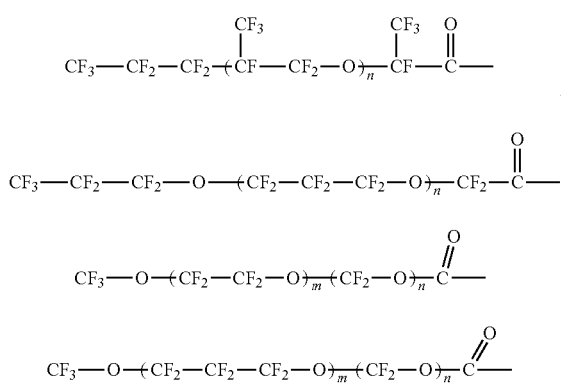

wherein, m and n each are independently positive integers, preferably m is 1-99 and n is 1-10.

In the present invention, m may be 1, 2, 3, 4, 5, 10, 15, 20, 25, 30, 40, 50, 60, 70, 80, 90, 99, and may be in a range therebetween. Similarly, n may be 1, 2, 3, 4, 5, 6, 7, 8, 9, 10, or may be in a range consisted of them.

In some embodiments, A is a group represented by formula K; and in other embodiments, A is a group represented by formula Z or D, and a value of m/n is 0.2-25, preferably 0.2-15, more preferably 0.2-10.

According to the lubricating oil friction modifier provided by the present invention, wherein, B may be a polyamine compound or a dendrimer. Correspondingly, $B^{y+}$ represents a polyamine cationic group or a dendrimer cationic group having x amino groups and y ammonium ions.

In the present invention, the term "polyamine compound" refers to an amine containing two or more amino groups in the molecule thereof. Examples of the polyamine compound suitable for use in the present invention include, but are not limited to: ethylenediamine, triethyldiamine, p-biphenyldiamine, 1,4-phenylenediamine, 1,4-phenylenedimethanamine and tri(2-aminoethyl)amine.

Examples of the dendrimer suitable for use in the present invention include, but are not limited to: a polyamide-amine type (PAMAM) dendrimer with ethylenediamine, triethyldiamine, p-biphenyldiamine, 1,4-phenylenediamine, 1,4-phenylenedimethanamine or tri(2-aminoethyl)amine as a core. The dendrimer has a generation number of preferably 0-10, more preferably 0-4, and most preferably 0-3. For example, B is a PAMAM dendrimer with ethylenediamine as a core, and has a generation number of 0 or 1.

According to the lubricating oil friction modifier provided by the present invention, wherein, in $A_xB^{y+}(C^-)_y$, $x+y\geq3$, preferably $x+y\geq4$.

According to the lubricating oil friction modifier provided by the present invention, wherein, B is a dendrimer, in $A_xB^{y+}(C^-)_y$, $x+y=2^{2+1}$; and d represents the generation number of the dendrimer. In some embodiments, the ratio of x to y is 1:3-3:1.

In some embodiments, if d is 0 or 1, x+y=4 or 8, wherein x has a range of preferably 2-6, and y has a range of preferably 2-6.

According to the lubricating oil friction modifier provided by the present invention, there is no special requirement for the positions of group A and $C^-$ anion on the cationic group $B^{y+}$ of the dendrimer.

For example, if B is a 0th generation PAMAM dendrimer, the lubricating oil friction modifier may have a structure represented by formulae I or II,

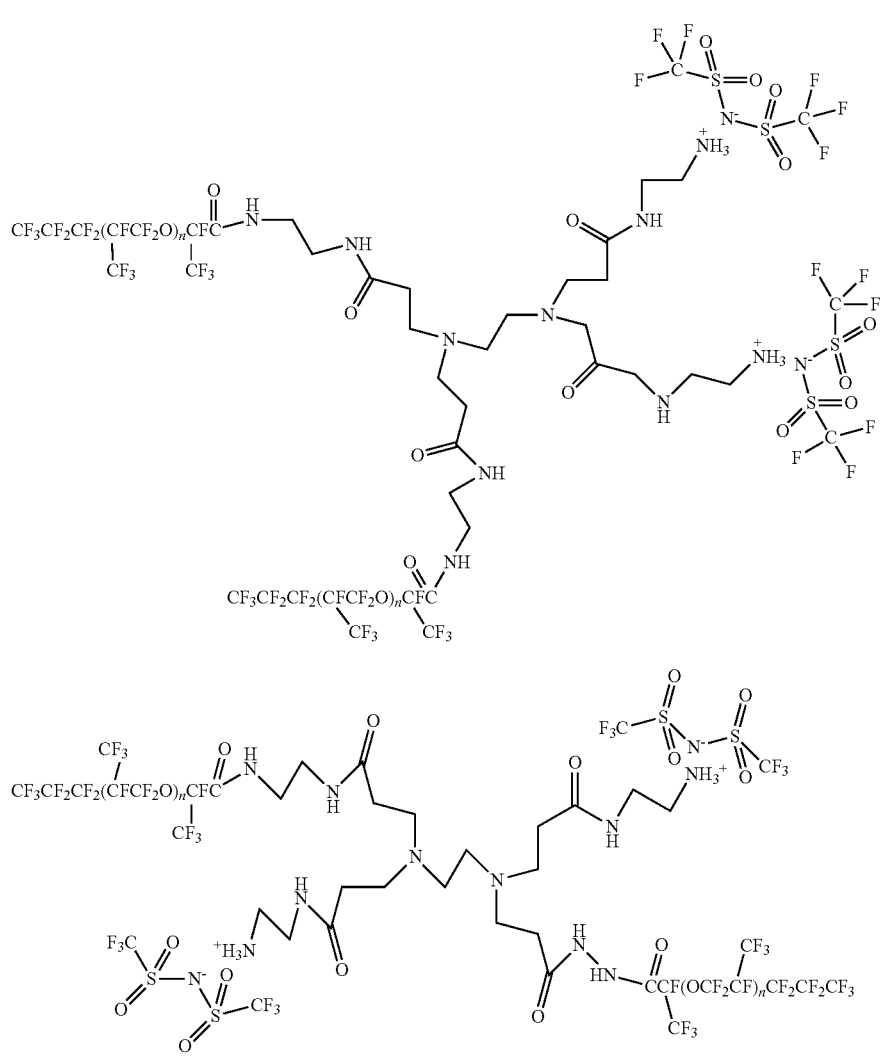

In a second aspect, the present invention provides a preparation method for lubricating oil friction modifier, wherein the preparation method comprises the following steps:

S100. Performing acylation reaction between a perfluoropolyether acylating agent and a polyamine compound or a dendrimer with an amino end group in the presence of solvent and promoter to obtain a solution of a first reaction product;

S200. adding an acid and a salt of at least one anion selected from $BF_4^-$, $PF_6^-$, trifluorotri(pentafluoroethyl) phosphate anion, bistrifluoromethylsulfonimide anion, $Mn_2O_4^-$, and $ClO_4^-$ to the solution of the first reaction product obtained in step S100, and stirring the reaction to obtain a solution of a second reaction product;

S300. neutralizing the solution of the second reaction product obtained in step S200, performing liquid separation, and removing the solvent therefrom to obtain a target product.

According to the preparation method provided by the present invention, wherein the perfluoropolyether acylating agent in step S100 is at least one acylating agent selected from the formulae K', Y', Z' and D',

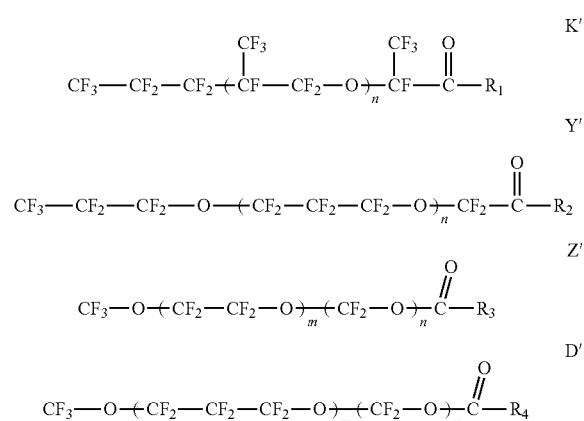

wherein, $R_1$, $R_2$, $R_3$, and $R_4$ each are independently fluorine, chlorine, bromine, anhydride, or hydroxyl group.

According to the preparation method provided by the present invention, wherein the polyamine compound in step S100 is selected from ethylenediamine, triethyldiamine, p-biphenyldiamine, 1,4-phenylenediamine, 1,4-phenylenedimethanamine and tri(2-aminoethyl)amine; and/or the dendrimer is a PAMAM dendrimer with ethylenediamine, triethyldiamine, p-biphenyldiamine, 1,4-phenylenediamine, 1,4-phenylenedimethanamine or tri(2-aminoethyl) amine as a core, and the dendrimer has a generation number of preferably 0-10, more preferably 0-4, and most preferably 0-3.

According to the preparation method provided by the present invention, wherein, a molar ratio of the perfluoropolyether acylating agent to the polyamine compound or the dendrimer in step S100 is x:1.

According to the preparation method provided by the present invention, wherein, the promoter in step S100 is pyridine and/or triethylamine. In the present invention, the promoter such as pyridine and/or triethylamine is used to promote the reaction.

According to the preparation method provided by the present invention, the solvent in step S100 is 1,1,2-trifluorotrichloroethane (F113). In the present invention, the solvent such as F113 is used to achieve a complete reaction.

According to the preparation method provided by the present invention, the step S100 comprises:
S101. mixing the perfluoropolyether acylating agent with the solvent and the promoter to obtain a mixture;
S102. adding the polyamine compound or the dendrimer with the amino group as the terminal group to the mixture obtained in step S101 at a temperature of −5 to 0° C., and refluxing to obtain a refluxing reaction product; and
S103. neutralizing the refluxing reaction product obtained in step S102, and performing liquid separation to obtain the solution of the first reaction product.

In some embodiments, in step S101, a mass ratio of the perfluoropolyether acylating agent in the mixture is 1:0.5 to 1:30, preferably 1:1 to 1:10.

According to the preparation method provided by the present invention, wherein a molar ratio of the salt to the polyamine compound or the dendrimer in step S200 is y:1. In some embodiments, a ratio of x to y is 1:3-3:1.

In some embodiments, the salt in step S200 is at least one selected from lithium salt, sodium salt, and potassium salt.

According to the preparation method provided by the present invention, wherein, a molar ratio of the acid to the salt in step S200 is 1:1 to 20:1, preferably 1:1 to 10:1.

In some embodiments, the acid is at least one selected from nitric acid, sulfuric acid, and hydrochloric acid.

According to the preparation method provided by the present invention, wherein, in each of steps S103 and S300, an aqueous solution containing at least one of sodium bicarbonate, potassium bicarbonate, sodium carbonate, potassium carbonate, sodium hydroxide and potassium hydroxide is independently used for neutralization.

In a third aspect, the present invention provides a lubricating oil friction modifier prepared by the preparation method.

In a fourth aspect, the present invention provides use of the lubricating oil friction modifier or the lubricating oil friction modifier prepared by the preparation method in lubricating oil.

In a fifth aspect, the present invention provides a lubricating oil composition, comprising 90-99 weight parts of a base lubricating oil and 1-10 weight parts of the lubricating oil friction modifier, wherein the base lubricating oil is at least one selected from fluorine oil and fluorine grease.

According to the lubricating oil composition provided by the present invention, wherein, the lubricating oil composition comprises 92-97 weight parts of the base lubricating oil and 3-8 weight parts of the lubricating oil friction modifier.

The present invention has the following advantages: the lubricating oil friction modifier of the present invention has a good solubility with fluorine oil and fluorine grease, will not precipitate in the fluorine oil and the fluorine grease after being added, and can significantly improve the wear resistance of a lubricating oil such as the fluorine oil and the fluorine grease.

BRIEF DESCRIPTION OF THE DRAWINGS

The FIGURE is a preparation scheme for a lubricating oil friction modifier according to an embodiment the present invention.

DETAILED DESCRIPTION OF THE EMBODIMENTS

In the following, the present invention will be further illustrated in combination with specific examples, which will not constitute any limitation on the present invention.

Example 1

Referring to the FIGURE, a lubricating oil friction modifier is prepared by the following method.

(1) 3 g of K-type perfluoropolyether acyl fluoride (provided by Sinopec Lubricant Co., Ltd., n=7), 1 mL pyridine, and 100 mL of F113 (1,1,2-trifluorotrichloroethane) were added into a 300 mL three-necked flask under stirring. Under a condition of −3° C., 2 g of a 0th generation PAMAM dendrimer (purchased from Weihai Chenyuan Organosilicone New Materials Co., Ltd., trade name: CYD-100A, with ethylenediamine as a core) was added dropwise. After completion of dropwise addition, the resultant was stirred for 1 h at −5 to 0° C. Then the resultant was subjected to gradual temperature rise and reacted under refluxing for 3 h, the heating was stopped. When the reaction temperature was lowered to 25-30° C., 150 mL of saturated sodium bicarbonate aqueous solution was added, the resultant was stirred for 5 min, and a lower-layer solution was collected through a separating funnel.

(2) 2 mL of nitric acid having a concentration of 98% was added into the above solution, the resultant was stirred at room temperature for 7 min, then 8 g of lithium bistrifluoromethylsulfonimide was added, the resultant was allowed to react under stirring for 5 h, and then the reaction was stopped. Then 150 mL of saturated sodium bicarbonate aqueous solution was added, the resultant was stirred at room temperature for 5 min, and a lower-layer solution was collected through a separating funnel. To this lower-layer solution, 150 mL of saturated sodium bicarbonate aqueous solution was further added, the resultant was stirred at room temperature for 5 min, and a lower-layer solution was collected through a separating funnel.

(3) After the F113 solvent was removed from the above lower-layer solution through vacuum distillation, 4 g of viscous liquid was obtained, which was as a target product.

The obtained product was characterized by infrared spectroscopy, wherein, 2929.69 $cm^{-1}$ and 1456.85-1305.25 $cm^{-1}$ are —$CH_2$ absorption peaks; 2375.19-2208.8 $cm^{-1}$ are amine salt absorption peaks; 1819.08 $cm^{-1}$ is a —C(O)— absorption peak; 1696.82 $cm^{-1}$ and 1635.98 $cm^{-1}$ are —C(O)NH— absorption peaks; and 1116.10 $cm^{-1}$ is a tertiary amine absorption peak.

Example 2

(1) 3 g of K-type perfluoropolyether acyl fluoride (provided by Sinopec Lubricant Co., Ltd., n=10), 1 mL pyridine, and 100 mL of F113 (1,1,2-trifluorotrichloroethane) were added into a 300 mL three-necked flask under stirring. Under a condition of −3° C., 1.5 g of a second generation PAMAM dendrimer (purchased from Weihai Chenyuan Organosilicone New Materials Co., Ltd., trade name: CYD-120A, with ethylenediamine as a core) was added dropwise. After completion of dropwise addition, the resultant was stirred for 1 h at −5 to 0° C. Then the resultant was subjected to gradual temperature rise and reacted under refluxing for 3 h, the heating was stopped. When the reaction temperature was lowered to 25-30° C., 150 mL of saturated sodium bicarbonate aqueous solution was added, the resultant was stirred for 5 min, and a lower-layer solution was collected through a separating funnel.

(2) 2 mL of nitric acid having a concentration of 98% was added into the above solution, the resultant was stirred at room temperature for 7 min, then 10 g of $BF_4Li$ was added, the resultant was allowed to react under stirring for 5 h, and then the reaction was stopped. Then 150 mL of saturated sodium bicarbonate aqueous solution was added, the resultant was stirred at room temperature for 5 min, and a lower-layer solution was collected through a separating funnel. To this lower-layer solution, 150 mL of saturated sodium bicarbonate aqueous solution was further added, the resultant was stirred at room temperature for 5 min, and a lower-layer solution was collected through a separating funnel.

(3) After the F113 solvent was removed from the above lower-layer solution through vacuum distillation, 3.8 g of viscous liquid was obtained, which was as a target product.

The obtained product was characterized by infrared spectroscopy, and the positions of individual peaks were substantially the same as those in Example 1.

Example 3

(1) 3 g of Z-type perfluoropolyether acyl fluoride (provided by Sinopec Lubricant Co., Ltd., m=2, n=10), 1 mL pyridine, and 100 mL of F113 (1,1,2-trifluorotrichloroethane) were added into a 300 mL three-necked flask under stirring. Under a condition of −3° C., 1.8 g of a first generation PAMAM dendrimer (purchased from Weihai Chenyuan Organosilicone New Materials Co., Ltd., trade name: CYD-110A, with triethyldiamine as a core) was added dropwise. After completion of dropwise addition, the resultant was stirred for 1 h at −5 to 0° C. Then the resultant was subjected to gradual temperature rise and reacted under refluxing for 3 h, the heating was stopped. When the reaction temperature was lowered to 25-30° C., 150 mL of saturated sodium bicarbonate aqueous solution was added, the resultant was stirred for 5 min, and a lower-layer solution was collected through a separating funnel.

(2) 2 mL of nitric acid having a concentration of 98% was added into the above solution, the resultant was stirred at room temperature for 7 min, then 10 g of $LiPF_6$ was added, the resultant was allowed to react under stirring for 5 h, and then the reaction was stopped. Then 150 mL of saturated sodium bicarbonate aqueous solution was added, the resultant was stirred at room temperature for 5 min, and a lower-layer solution was collected through a separating funnel. To this lower-layer solution, 150 mL of saturated sodium bicarbonate aqueous solution was further added, the resultant was stirred at room temperature for 5 min, and a lower-layer solution was collected through a separating funnel.

(3) After the F113 solvent was removed from the above lower-layer solution through vacuum distillation, 4.5 g of viscous liquid was obtained, which was as a target product.

The obtained product was characterized by infrared spectroscopy, and the positions of individual peaks were substantially the same as those in Example 1.

Example 4

(1) 3 g of D-type perfluoropolyether acyl fluoride (provided by Sinopec Lubricant Co., Ltd., n=8), 1 mL pyridine, and 100 mL of F113 (1,1,2-trifluorotrichloroethane) were added into a 300 mL three-necked flask under stirring. Under a condition of −3° C., 1.5 g of a third generation PAMAM dendrimer (purchased from Weihai Chenyuan Organosilicone New Materials Co., Ltd., trade name: CYD-130A, with p-biphenyldiamine as a core) was added dropwise. After completion of dropwise addition, the resultant was stirred for 1 h at −5 to 0° C. Then the resultant was subjected to gradual temperature rise and reacted under refluxing for 3 h, the heating was stopped. When the reaction temperature was lowered to 25-30° C., 150 mL of saturated sodium bicarbonate aqueous solution was added, the resultant was stirred for 5 min, and a lower-layer solution was collected through a separating funnel.

(2) 2 mL of nitric acid having a concentration of 98% was added into the above solution, the resultant was stirred at room temperature for 7 min, then 14 g of $LiAsF_6$ was added, the resultant was allowed to react under stirring for 5 h, and then the reaction was stopped. Then 150 mL of saturated sodium bicarbonate aqueous solution was added, the resultant was stirred at room temperature for 5 min, and a lower-layer solution was collected through a separating funnel. To this lower-layer solution, 150 mL of saturated sodium bicarbonate aqueous solution was further added, the resultant was stirred at room temperature for 5 min, and a further lower-layer solution was collected through a separating funnel.

(3) After the F113 solvent was removed from the above lower-layer solution through vacuum distillation, 4.2 g of viscous liquid was obtained, which was as a target product.

The obtained product was characterized by infrared spectroscopy, and the positions of individual peaks were substantially the same as those in Example 1.

Example 5

(1) 3 g of Y-type perfluoropolyether acyl fluoride (provided by Sinopec Lubricant Co., Ltd., n=8), 1 mL triethylamine, and 100 mL of F113 (1,1,2-trifluorotrichloroethane) were added into a 300 mL three-necked flask under stirring. Under a condition of −3° C., 4 g of tri(2-aminoethyl)amine (purchased from Aladdin Reagent Co., Ltd.) was added dropwise. After completion of dropwise addition, the resultant was stirred for 1 h at −5 to 0° C. Then the resultant was subjected to gradual temperature rise and reacted under refluxing for 3 h, the heating was stopped. When the reaction temperature was lowered to 25-30° C., 150 mL of saturated sodium bicarbonate aqueous solution was added, the resultant was stirred for 5 min, and a lower-layer solution was collected through a separating funnel.

(2) 2 mL of nitric acid having a concentration of 98% was added into the above solution, the resultant was stirred at room temperature for 7 min, then 8 g of lithium bistrifluoromethylsulfonimide was added, the resultant was allowed to react under stirring for 5 h, and then the reaction was stopped. Then 150 mL of saturated sodium bicarbonate aqueous solution was added, the resultant was stirred at room temperature for 5 min, and a lower-layer solution was collected through a separating funnel. To this lower-layer solution, 150 mL of saturated sodium bicarbonate aqueous solution was further added, the resultant was stirred at room temperature for 5 min, and a lower-layer solution was collected through a separating funnel.

(3) After the F113 solvent was removed from the above lower-layer solution through vacuum distillation, 3.8 g of viscous liquid was obtained, which was as a target product.

The obtained product was characterized by infrared spectroscopy, and the positions of individual peaks were substantially the same as those in Example 1.

Example 6

(1) 3 g of Y-type perfluoropolyether acyl fluoride (provided by Sinopec Lubricant Co., Ltd., n=8), 1 mL triethylamine, and 100 mL of F113 (1,1,2-trifluorotrichloroethane) were added into a 300 mL three-necked flask under stirring. Under a condition of −3° C., 4.2 g of 1,4-phenylenedimethanamine (purchased from Aladdin Reagent Co., Ltd.) was added dropwise. After completion of dropwise addition, the resultant was stirred for 1 h at −5 to 0° C. Then the resultant was subjected to gradual temperature rise and reacted under refluxing for 3 h, the heating was stopped. When the reaction temperature was lowered to 25-30° C., 150 mL of saturated sodium bicarbonate aqueous solution was added, the resultant was stirred for 5 min, and a lower-layer solution was collected through a separating funnel.

(2) 2 mL of nitric acid having a concentration of 98% was added into the above solution, the resultant was stirred at room temperature for 7 min, then 9 g of $BF_4Li$ was added, the resultant was allowed to react under stirring for 5 h, and then the reaction was stopped. Then 150 mL of saturated sodium bicarbonate aqueous solution was added, the resultant was stirred at room temperature for 5 min, and a lower-layer solution was collected through a separating funnel. To this lower-layer solution, 150 mL of saturated sodium bicarbonate aqueous solution was further added, the resultant was stirred at room temperature for 5 min, and a lower-layer solution was collected through a separating funnel.

(3) After the F113 solvent was removed from the above lower-layer solution through vacuum distillation, 4.1 g of viscous liquid was obtained, which was as a target product.

The obtained product was characterized by infrared spectroscopy, wherein, 3010 $cm^{-1}$ is an H absorption peak on a benzene ring; 2929.42 $cm^{-1}$ is a —$CH_2$ absorption peak; 2372.31-2205.32 $cm^{-1}$ are amine salt absorption peaks; 1821.05 $cm^{-1}$ is a —C(O)— absorption peak; 1692.48 $cm^{-1}$ and 1632.75 $cm^{-1}$ are —C(O)NH— absorption peaks; 1460 $cm^{-1}$, 1500 $cm^{-1}$ and 1600 $cm^{-1}$ are benzene ring absorption peaks; and 1116.10 $cm^{-1}$ is a tertiary amine absorption peak.

Application Example 1

(1) A friction and wear test was conducted on a fluorine oil (provided by Sinopec Lubricant Co., Ltd., a fluoric vacuum pump oil) by using an HFRR instrument under the following test conditions: ball/disc friction pair, 200 g, 80 Hz, 90° C., 1 h, 1 mm. The measured average friction coefficient was 0.122, the measured disc wear volume was 1.295*$10^6$ $\mu m^3$, and the measured disc wear rate was 0.144*$10^{-6}$ $mm^2$/gs.

(2) 3 g of the lubricating oil friction modifier from Example 1 was added to 97 g of fluorine oil (provided by Sinopec Lubricant Company, a fluoric vacuum pump oil). A friction and wear test was conducted on the resultant by using an HFRR instrument under the following test conditions: ball/disc friction pair, 200 g, 80 Hz, 90° C., 1 h, 1 mm. The measured average friction coefficient was 0.118, the measured disc wear volume was 7.18*$10^5$ $\mu m^3$, and the measured disc wear rate was 0.0798*$10^{-6}$ $mm^2$/gs.

Compared with a single fluorine oil, the fluorine oil added with 3% of the lubricating oil friction modifier had a slightly reduced friction coefficient, but its disc wear rate was significantly reduced by 44.58%. Thus it can be seen that, the fluorine oil added with the prepared lubricating oil friction modifier had a significantly improved wear resistance.

Application Example 2

(1) A friction and wear test was conducted on a fluorine oil (provided by Sinopec Lubricant Co., Ltd., an FM 110 shielding oil for coating) by using an HFRR instrument under the following test conditions: ball/disc friction pair, 200 g, 80 Hz, 90° C., 1 h, 1 mm. The measured average friction coefficient was 0.122, the measured disc wear volume was 1.295*$10^6$ $\mu m^3$, and the measured disc wear rate was 0.144*$10^{-6}$ $mm^2$/gs.

(2) 5 g of the lubricating oil friction modifier from Example 2 was added to 95 g of fluorine oil (provided by Sinopec Lubricant Co., Ltd., an FM 110 shielding oil for coating). A friction and wear test was conducted on the resultant by using an HFRR instrument under the following test conditions: ball/disc friction pair, 200 g, 80 Hz, 90° C., 1 h, 1 mm. The measured average friction coefficient was 0.115, the measured disc wear volume was 6.77*$10^5$ $\mu m^3$, and the measured disc wear rate was 0.0752*$10^{-6}$ $mm^2$/gs.

Compared with a single fluorine oil, the fluorine oil added with 5% of the lubricating oil friction modifier had a slightly reduced friction coefficient, but its disc wear rate was significantly reduced by 47.78%. Thus it can be seen that, the fluorine oil added with the prepared lubricating oil friction modifier had a significantly improved wear resistance.

Application Example 3

(1) A friction and wear test was conducted on a fluorine grease (provided by Sinopec Lubricant Co., Ltd., a high temperature resistant lubricating grease) by using an HFRR instrument under the following test conditions: ball/disc friction pair, 200 g, 50 Hz, 90° C., 1 h, 2 mm. The measured average friction coefficient was 0.142, and the measured diameter of disc wear spot was 126 μm.

(2) 8 g of the lubricating oil friction modifier from Example 3 was added to 92 g of the fluorine grease (provided by Sinopec Lubricant Co., Ltd., a high temperature resistant lubricating grease). A friction and wear test was conducted on the resultant by using an HFRR instrument under the following test conditions: ball/disc friction pair, 200 g, 50 Hz, 90° C., 1 h, 2 mm. The measured average friction coefficient was 0.115, and the measured diameter of disc wear spot was 92 μm.

Compared with a single fluorine grease, the fluorine grease added with 8% of the lubricating oil modifier had a friction coefficient and a diameter of disc wear spot significantly reduced by 19.01% and 26.98%, respectively. Thus it can be seen that, the fluorine grease added with the prepared lubricating oil friction modifier had a significantly improved friction and wear resistance.

Application Example 4

(1) A friction and wear test was conducted on a fluorine grease (provided by Sinopec Lubricant Co., Ltd., a high temperature resistant lubricating grease) by using an HFRR instrument under the following test conditions: ball/disc friction pair, 200 g, 50 Hz, 90° C., 1 h, 2 mm. The measured average friction coefficient was 0.142, and the measured diameter of disc wear spot was 126 μm.

(2) 9 g of the lubricating oil friction modifier from Example 4 was added to 91 g of the fluorine grease (provided by Sinopec Lubricant Co., Ltd., a high temperature resistant lubricating grease). A friction and wear test was conducted on the resultant by using an HFRR instrument under the following test conditions: ball/disc friction pair, 200 g, 50 Hz, 90° C., 1 h, 2 mm. The measured average friction coefficient was 0.108, and the measured diameter of disc wear spot was 87 μm.

Compared with a single fluorine grease, the fluorine grease added with 9% of the lubricating oil modifier had a friction coefficient and a diameter of disc wear spot significantly reduced by 23.94% and 30.95%, respectively. Thus it can be seen that, the fluorine grease added with the prepared lubricating oil friction modifier had a significantly improved friction and wear resistance.

Application Example 5

(1) A friction and wear test was conducted on a fluorine oil (provided by Sinopec Lubricant Co., Ltd., an FM 110 shielding oil for coating) by using an HFRR instrument under the following test conditions: ball/disc friction pair, 200 g, 80 Hz, 90° C., 1 h, 1 mm. The measured average friction coefficient was 0.122, the measured disc wear volume was $1.295*10^6$ μm$^3$, and the measured disc wear rate was $0.144*10^{-6}$ mm$^2$/gs.

(2) 10 g of the lubricating oil friction modifier from Example 5 was added to 90 g of the fluorine oil (provided by Sinopec Lubricant Co., Ltd., an FM 110 shielding oil for coating). A friction and wear test was conducted on the resultant by using an HFRR instrument under the following test conditions: ball/disc friction pair, 200 g, 80 Hz, 90° C., 1 h, 1 mm. The measured average friction coefficient was 0.112, the measured disc wear volume was $7.87*10^5$ μm$^3$, and the measured disc wear rate was $0.0874*10^{-6}$ mm$^2$/gs.

Compared with a single fluorine oil, the fluorine oil added with 10% of the lubricating oil friction modifier had a slightly reduced friction coefficient, but its disc wear rate was significantly reduced by 39.28%. Thus it can be seen that, the fluorine oil added with the prepared lubricating oil friction modifier had a significantly improved wear resistance.

Application Example 6

(1) A friction and wear test was conducted on a fluorine oil (provided by Sinopec Lubricant Co., Ltd., an FM 110 shielding oil for coating) by using an HFRR instrument under the following test conditions: ball/disc friction pair, 200 g, 80 Hz, 90° C., 1 h, 1 mm. The measured average friction coefficient was 0.122, the measured disc wear volume was $1.295*10^6$ μm$^3$, and the measured disc wear rate was $0.144*10^{-6}$ mm$^2$/gs.

(2) 1 g of the lubricating oil friction modifier from Example 6 was added to 95 g of the fluorine oil (provided by Sinopec Lubricant Co., Ltd., an FM 110 shielding oil for coating). A friction and wear test was conducted on the resultant by using an HFRR instrument under the following test conditions: ball/disc friction pair, 200 g, 80 Hz, 90° C., 1 h, 1 mm. The measured average friction coefficient was 0.117, the measured disc wear volume was $9.87*1105$ μm$^3$, and the measured disc wear rate was $0.0874*10^{-6}$ mm$^2$/gs.

Compared with a single fluorine oil, the fluorine oil added with 1% of the lubricating oil friction modifier had a slightly reduced friction coefficient, but its disc wear rate was significantly reduced by 23.84%. Thus it can be seen that, the fluorine oil added with the prepared lubricating oil friction improver had a significantly improved wear resistance.

As to any numerical value mentioned in the present invention, if there is only a two-unit interval between any lowest value and any highest value, it includes all the values obtained by increasing by one unit each time from the lowest value to the highest value. For example, if it is claimed that an amount of a component, or a value of a process variable such as temperature, pressure, time, etc. is 50-90, it means that values such as 51-89, 52-88 . . . , 69-71, 70-71, etc. are specifically enumerated in the description. As to non-integer values, it is appropriate to consider using 0.1, 0.01, 0.001, or 0.0001 as one unit. These are only some specially specified examples. In the present application, likewise, all the possible combinations of the enumerated values between a lowest value and a highest value are considered to have been disclosed.

It should be noted that, the examples described above are only used to explain the present invention, but do not constitute any limitation on the present invention. The present invention has been described by referring to typical examples, but it should be understood that the words used herein are descriptive and explanatory vocabularies, rather than restrictive vocabularies. Modifications may be made to the present invention within the scope of the claims of the present invention as required, and revisions may be made without departing from the scope and spirit of the present invention. Although the present invention described herein relates to specific methods, materials, and examples, but it is not meant that the present invention is limited to the specific examples disclosed herein. On the contrary, the present invention may be extended to all the other methods and applications with the same functionality.

The invention claimed is:

1. A lubricating oil friction modifier, having a chemical formula of $A_xB^{y+}(C^-)_y$, wherein, A represents a perfluoropolyether acyl group, $B^{y+}$ represents a cationic group having x amino groups and y ammonium ions, $C^-$ is $BF_4^-$ (boron tetrafluoride anion), $PF_6^-$ (hexafluorophosphate anion), $AsF_6^-$ (hexafluoroarsenate anion), FAP$^-$ (trifluorotri(pentafluoroethyl)phosphate anion), TFSI$^-$ (bistrifluoromethylsulfonimide anion), $Mn_2O_4^-$ (manganate), or $ClO_4^-$ (perchlorate), x is an integer greater than or equal to 1, y is an integer greater than or equal to 1, and x+y≥2.

2. The lubricating oil friction modifier according to claim 1, wherein, A is a group of formula K, Y, Z, or D:

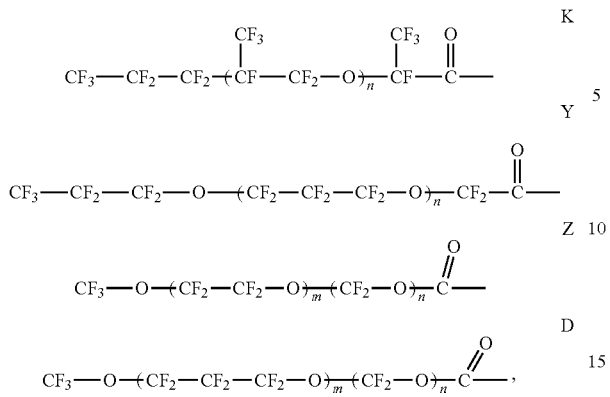

wherein m and n each are independently positive integers, m is 1-99, and n is 1-10.

3. The lubricating oil friction modifier according to claim 1, wherein B is a polyamine compound or a dendrimer;
wherein the polyamine compound is selected from ethylenediamine, triethyldiamine, p-biphenyldiamine, 1,4-phenylenediamine, 1,4-phenylenedimethanamine and tri(2-aminoethyl)amine;
the dendrimer is a PAMAM dendrimer having a core selected from ethylenediamine, triethyldiamine, p-biphenyldiamine, 1,4-phenylenediamine, 1,4-phenylenedimethanamine, and tri(2-aminoethyl)amine, and has a generation number of 0 to 10.

4. The lubricating oil friction modifier according to claim 3, wherein, in $A_xB^{y+}(C^-)_y$, $x+y≥3$.

5. A preparation method for the lubricating oil friction modifier of claim 1, comprising:
S100, performing acylation reaction between a perfluoropolyether acylating agent and a polyamine compound or a dendrimer with an amino end group in the presence of a solvent and a promoter to obtain a solution of a first reaction product;
S200, adding an acid and a salt of at least one anion selected from $BF_4^-$, $PF_6^-$, trifluorotri(pentafluoroethyl) phosphate anion, bistrifluoromethylsulfonimide anion, $Mn_2O_4^-$, and $ClO_4^-$ to the solution of the first reaction product obtained in step S100 to obtain a solution of a second reaction product; and
S300, neutralizing the solution of the second reaction product obtained in step S200, performing liquid separation, and removing the solvent therefrom to obtain a target product.

6. The preparation method according to claim 5, wherein, the perfluoropolyether acylating agent in step S100 is at least one acylating agent selected from acylating agents of formulae K', Y', Z' and D',

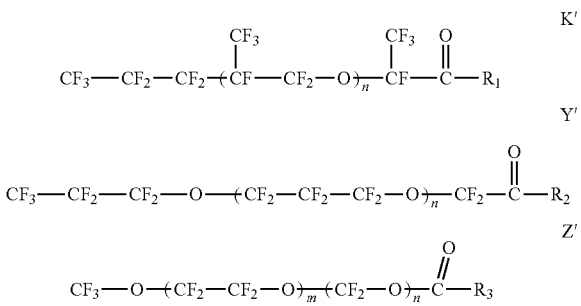

wherein, $R_1$, $R_2$, $R_3$ and $R_4$ each are independently fluorine, chlorine, bromine, anhydride, or hydroxyl group; and/or
the polyamine compound in step S100 is selected from ethylenediamine, triethyldiamine, p-biphenyldiamine, 1,4-phenylenediamine, 1,4-phenylenedimethanamine and tri(2-aminoethyl)amine; and/or the dendrimer is a PAMAM dendrimer having the core selected from ethylenediamine, triethyldiamine, p-biphenyldiamine, 1,4-phenylenediamine, 1,4-phenylenedimethanamine, and tri(2-aminoethyl)amine, and has a generation number of 0 to 10; and/or
the promoter in step S100 is pyridine, triethylamine, or a mixture thereof; and/or
the solvent in step S100 is 1,1,2-trifluorotrichloroethane; and/or
the step S100 further comprises:
S101, mixing the perfluoropolyether acylating agent with the solvent and the promoter to obtain a mixture;
S102, adding the polyamine compound or the dendrimer with the amino group as the terminal group to the mixture obtained in step S101 at a temperature of −5 to 0° C.; and refluxing to obtain a refluxing reaction product; and
S103, neutralizing the refluxing reaction product obtained in step S102, and performing liquid separation to obtain the solution of the first reaction product.

7. The preparation method according to claim 5, wherein the salt in step S200 is at least one selected from lithium salt, sodium salt, and potassium salt; and/or
the acid in step S200 is at least one selected from nitric acid, sulfuric acid, and hydrochloric acid; and/or
in each of steps S103 and S300, an aqueous solution containing at least one of sodium bicarbonate, potassium bicarbonate, sodium carbonate, potassium carbonate, sodium hydroxide and potassium hydroxide is independently used for neutralization.

8. A lubricating oil composition, comprising 90-99 weight parts of a base lubricating oil and 1-10 weight parts of the lubricating oil friction modifier of claim 1, wherein the base lubricating oil is at least one selected from fluorine oil and fluorine grease.

9. The lubricating oil composition according to claim 8, wherein the lubricating oil composition comprises 92-97 weight parts of the base lubricating oil and 3-8 weight parts of the lubricating oil friction improver.

10. The lubricating oil friction modifier according to claim 2, wherein A is a group of formula Z or D, and a value of m/n is 0.2-25.

11. The lubricating oil friction modifier according to claim 10, wherein the value of m/n is 0.2-15.

12. The lubricating oil friction modifier according to claim 10, wherein the value of m/n is 0.2-10.

13. The lubricating oil friction modifier according to claim 3, wherein the dendrimer has a generation number 0 to 4.

14. The lubricating oil friction modifier according to claim 3, wherein the dendrimer has a generation number 0 to 3.

15. The lubricating oil friction modifier according to claim 4, wherein, in $A_xB^{y+}(C^-)_y$, $x+y≥4$.

16. The lubricating oil friction modifier according to claim 4, wherein B is a dendrimer, and in $A_xB^{y+}(C^-)_y$, $x+y=2^{2+d}$, d is a number of generation of the dendrimer, and wherein d is 0 or 1, x is in a range of 2-6, and y is in a range of 2-6.

17. The preparation method according to claim 6, wherein the dendrimer has a generation number 0 to 4.

18. The preparation method according to claim 6, wherein, the dendrimer has a generation number of 0 to 3.

* * * * *